(12) United States Patent
Yeh

(10) Patent No.: US 9,409,007 B2
(45) Date of Patent: Aug. 9, 2016

(54) ASSEMBLING A NEEDLELESS VALVE SYSTEM

(75) Inventor: Jonathan Yeh, Diamond Bar, CA (US)

(73) Assignee: CareFusion 303, Inc., San Diego, CA (US)

( * ) Notice: Subject to any disclaimer, the term of this patent is extended or adjusted under 35 U.S.C. 154(b) by 406 days.

(21) Appl. No.: 13/359,332

(22) Filed: Jan. 26, 2012

(65) Prior Publication Data

US 2013/0193359 A1 Aug. 1, 2013

(51) Int. Cl.
*A61M 39/22* (2006.01)
*A61M 39/26* (2006.01)
*A61M 39/10* (2006.01)
*A61M 39/24* (2006.01)

(52) U.S. Cl.
CPC .............. *A61M 39/22* (2013.01); *A61M 39/26* (2013.01); *A61M 2039/1027* (2013.01); *A61M 2039/2433* (2013.01); *A61M 2207/00* (2013.01); *Y10T 29/49412* (2015.01)

(58) Field of Classification Search
CPC ........... A61M 39/22; A61M 2207/00; A61M 2039/1027; A61M 2039/2433; Y10T 29/49412
USPC ............. 251/149.7, 149, 149.4, 149.5, 149.8, 251/149.1; 604/256
See application file for complete search history.

(56) References Cited

U.S. PATENT DOCUMENTS

| 5,441,487 | A | 8/1995 | Vedder | |
| 7,241,285 | B1 | 7/2007 | Dikeman | |
| 7,520,489 | B2 * | 4/2009 | Ruschke et al. | 251/149.7 |
| 8,015,990 | B2 * | 9/2011 | Pascal et al. | 137/15.18 |
| 8,038,123 | B2 * | 10/2011 | Ruschke et al. | 251/149.7 |
| 8,298,196 | B1 * | 10/2012 | Mansour | 604/256 |
| 2009/0184275 | A1 | 7/2009 | Ruschke et al. | |
| 2010/0036330 | A1 * | 2/2010 | Plishka et al. | 604/256 |
| 2010/0308251 | A1 * | 12/2010 | Pascal et al. | 251/324 |

FOREIGN PATENT DOCUMENTS

| WO | 2010028044 A1 | 3/2010 |
| WO | 2011119347 A2 | 9/2011 |

OTHER PUBLICATIONS

Jarvis; William R., et al., "Health Care-Associated Bloodstream Infections Associated with Negative- or Positve-Pressure or Displacement Mechanical Valve Needleless Connectors," Clin. Infect. Dis., Dec. 15, 2009, vol. 49, No. 212, pp. 1821-1827.
International Search Report and Written Opinion for International Application No. PCT/US2013/021970 mailed May 15, 2013.
International Preliminary Report on Patentability in PCT Application No. PCT/US2013/021970 dated Jul. 29, 2014.
Extended European Search Report for Application No. 13741365.4, dated Jun. 16, 2015, 6 pages.

* cited by examiner

*Primary Examiner* — Craig Schneider
*Assistant Examiner* — Andrew J Rost
(74) *Attorney, Agent, or Firm* — McDermott Will & Emery LLP

(57) ABSTRACT

A base portion for a needleless valve system comprising a body, and a valve coupling feature disposed on the body. The valve coupling feature is configured for coupling to a base coupling feature of a valve of a first type and a base coupling feature of a valve of a second type.

14 Claims, 6 Drawing Sheets

ASSEMBLING A NEEDLELESS VALVE SYSTEM

BACKGROUND

Needleless valve systems have various components such as, but not limited to, a housing, valve portion and a base portion. Moreover, different types of needleless valve systems (e.g., positive displacement, negative displacement) require different types of components. Accordingly, a manufacturer of the needleless valve systems is unable to use components designed for one type needleless valve system for assembling the other type of needleless valve system.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1A:
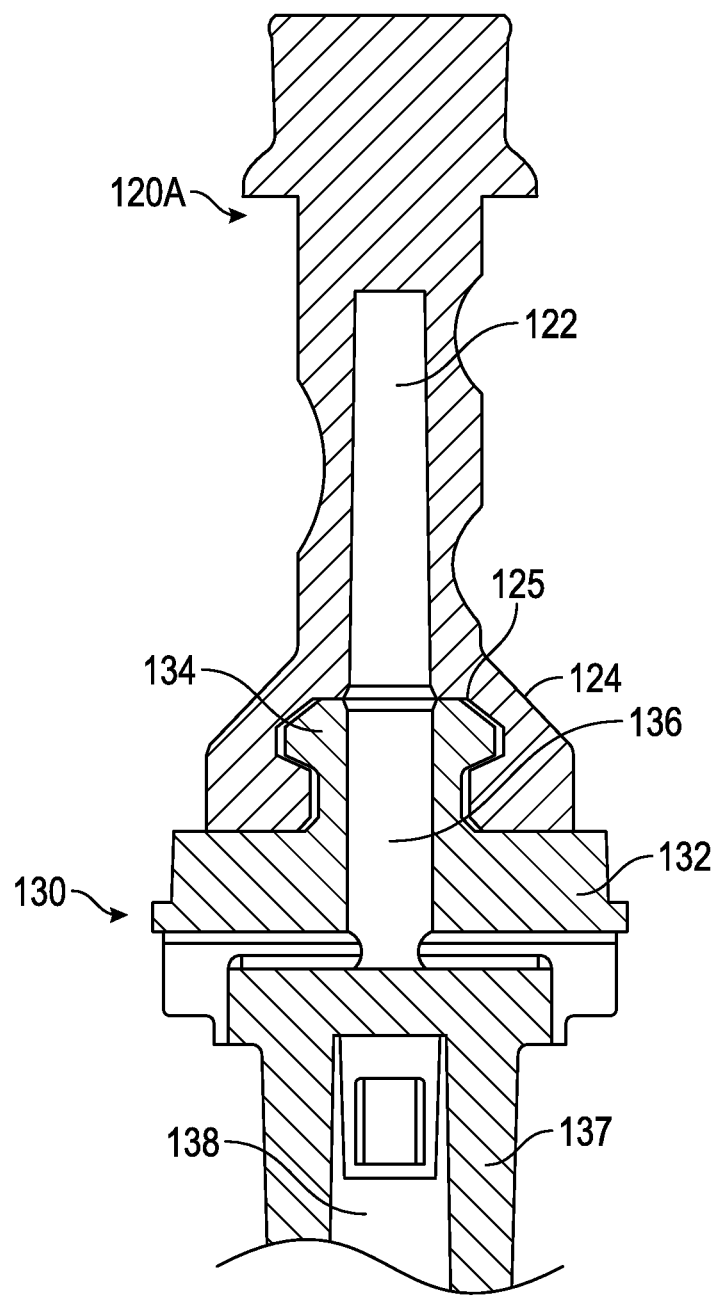
FIG. 1A illustrates an embodiment of a base portion and a first type of valve.
Figure 1B:
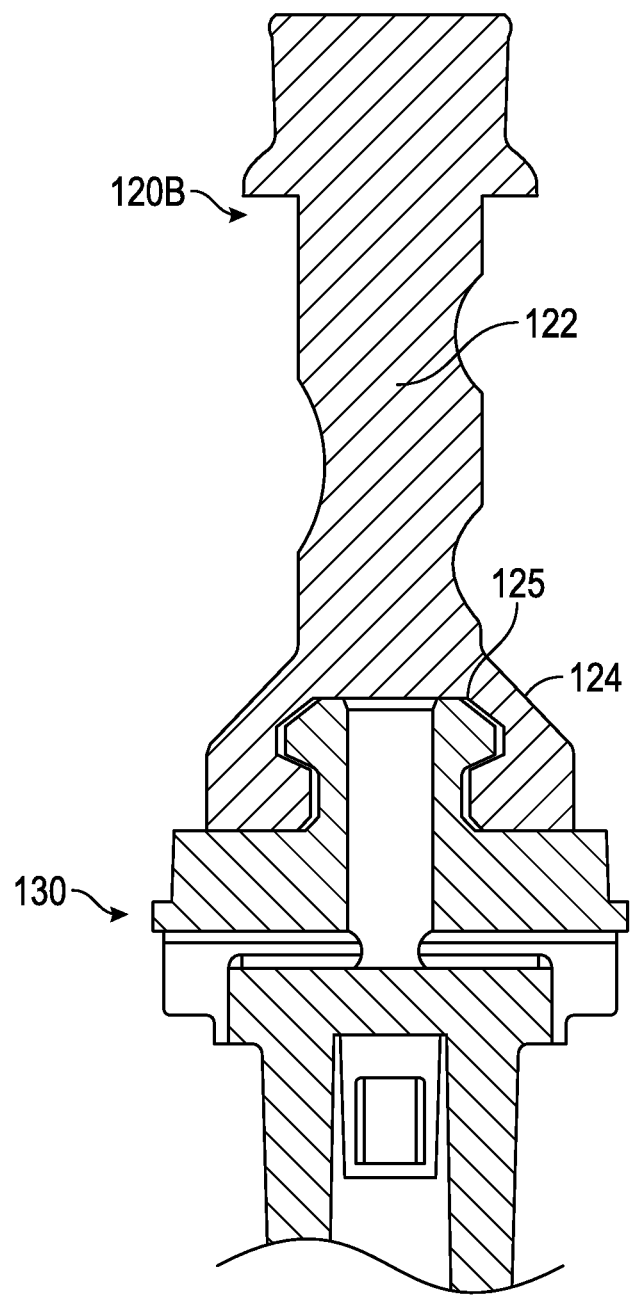
FIG. 1B illustrates an embodiment of a base portion and a second type of valve.

FIGS. 1A-B depicts embodiments of cross-sectional views of base portion 130 coupled to different types of valves. In particular, FIG. 1A depicts base portion 130 coupled to positive displacement valve 120A and FIG. 1B depicts base portion 130 coupled to negative displacement valve 120B. Therefore, base portion 130 can be used for assembly of both a positive displacement needleless valve system and a negative displacement needleless valve system, which will be described in further detail below.

In general, a positive displacement needleless valve expels fluid upon the disconnection of the needleless valve with a medical device (e.g., needleless syringe, catheter, etc.) by way of air within air channels 122 and 136, which will be described in detail below. In contrast, a negative displacement valve does not include air channel 122 and therefore, does not expel fluid upon the disconnection of the needleless valve with a medical device.

In reference to FIGS. 1A-B, base portion 130 includes body 132, valve coupling feature 134, air channel (or chamber) 136, interface 137 and port 138.

Components of base portion 130 may be coupled together or may be integral. For example, valve coupling feature 134, body 132 and interface 137, may be a single molded piece or may be separate components coupled together. In one embodiment, base portion 130 is comprised of a rigid material (e.g., polycarbonate).

Valve coupling feature 134 is configured to facilitate in the coupling of base portion 130 with different types of valves, for example, positive displacement valve 120A and negative displacement valve 120B.

As depicted, valve coupling feature 134 protrudes from body 132 and includes features that retain valve 120A. In such an embodiment, valve coupling feature 134 matingly corresponds to base retaining feature 125 disposed in the base portion 124 of valve 120A.

For example, valve 120A is disposed of a resilient material. Therefore, base portion 124 is able to resiliently expand and then contract around valve coupling feature 134 such that base coupling feature 125 mates with corresponding valve coupling feature 134. Accordingly, base portion 130 and valve 120A are coupled together for assembly in a needleless valve system.

Similarly, valve 120B may also be coupled to base portion 130 in the same manner as described above. In particular, valve 120B includes at least the same base portion 124 and base coupling feature 125 as valve 120A. In various embodiments, positive displacement valve 120A and negative displacement valve 120B are identical except that positive displacement valve 120A includes air channel 122 and negative displacement valve 120B does not. However, it should be appreciated that positive displacement valve 120A and negative displacement valve 120B may be physically different from one another (e.g., shape of the body, material, etc.)

It should be appreciated that the coupling of base portion 130 to positive displacement valve 120A or negative displacement valve 120B can be achieved in by various coupling means. For example, coupling can be achieved via various snap-fit configurations, threads, etc.

Air channel 136 is configured to pneumatically associate with air channel 122 when base portion 130 and positive displacement valve 120A are coupled together. In one embodiment, air channel 136 and air channel 122 are coaxial and have the same diameter.

Figure 2:
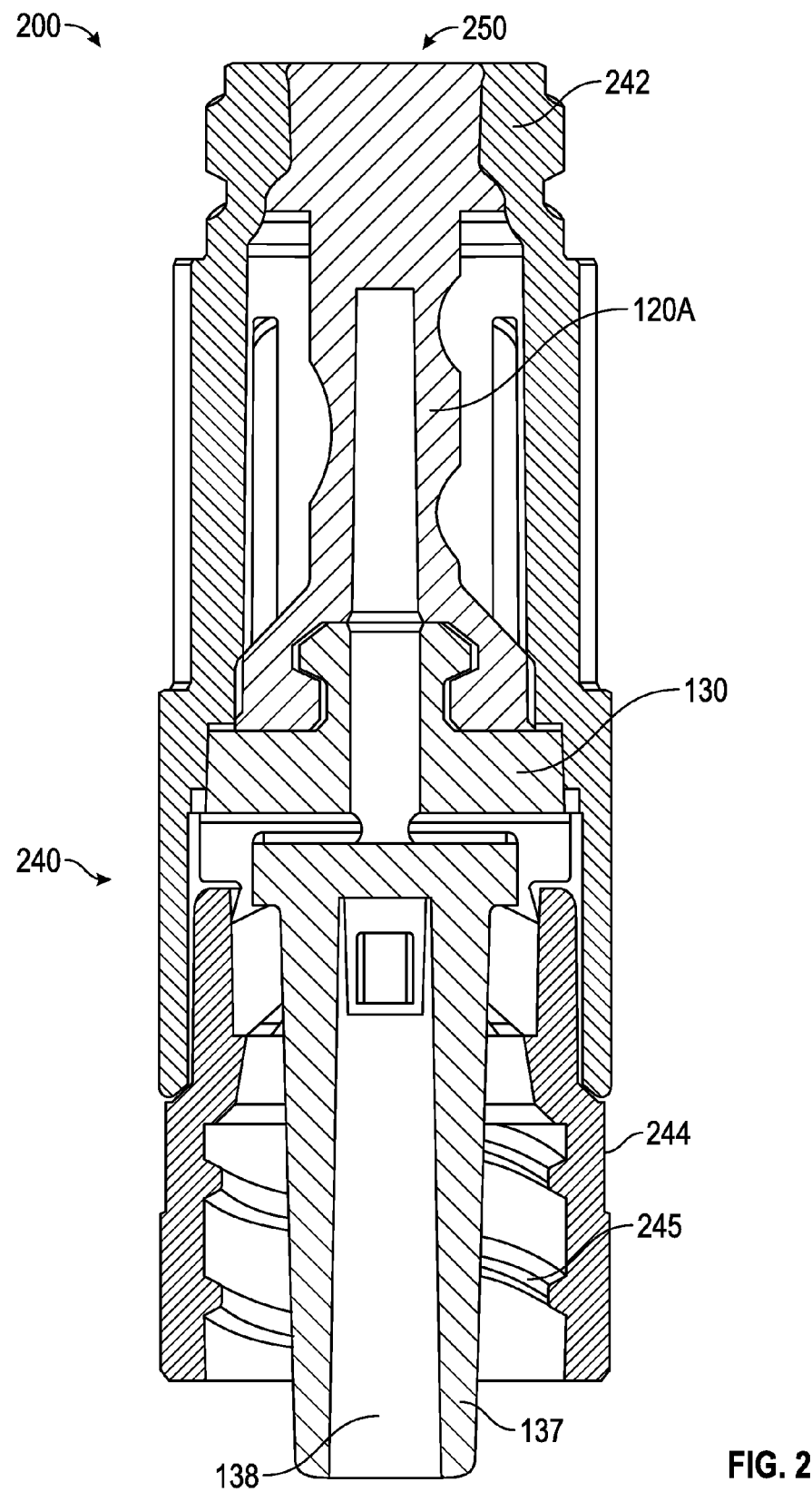
FIG. 2 illustrates an embodiment of a needleless valve system.

FIG. 2 depicts an embodiment of a cross-sectional view of needleless valve system 200. Needleless valve system 200 includes a sub-assembly of base portion 130 and positive displacement valve 120A. However, in one embodiment, needleless valve system 200 includes negative displacement valve 120B.

Therefore, needleless valve system 200 can be assembled to be a positive displacement needleless valve system or a negative displacement needleless valve system requiring only one type of base portion (e.g., base portion 130) that may be coupled to either positive displacement valve 120A or negative displacement valve 120B.

For purposes of clarity and brevity, the discussion regarding needleless valve system 200 will be directed towards a positive displacement needleless valve system.

Needleless valve system 200 also includes housing 240. Accordingly, housing 240 includes the sub-assembly of base portion 130 and positive displacement valve 120A (coupled together). Base portion 130 and housing 240 are coupled together such that base portion 130 and positive displacement valve 120A are retained within housing 240. Moreover, base portion 130 and housing 240 are sealed together such that the seal is air tight and water tight.

Housing 240 and base portion 130 may be coupled together by a various of coupling means. For example, the coupling may be achieved by adhesive, ultrasonic welding, etc.

Housing 240 includes fitting 244 for mating with another medical device, such as a catheter. In particular, fitting 244 includes female luer fitting 245. It should be appreciated that fitting 244 may be a separate component that is coupled to housing 240 or may be integral with housing 240. In one embodiment, housing 240 also include male luer fitting 242 for mating with female luer fitting of a medical device (e.g., needleless syringe).

During use of needleless valve system 200, a medical device compresses positive displacement valve 120A within housing 240, thereby breaking the seal between the housing and positive displacement valve 120A. Fluid is then conveyed through housing 240.

For example, a male luer of a needleless syringe is inserted through port 250 and compresses positive displacement valve 120A within housing 240. A fluid is conveyed from the needleless syringe around compressed positive displacement valve 120A and through port 138 to a catheter (not shown).

In the alternative, a male luer of a needleless syringe is inserted through port 250 and compresses positive displacement valve 120A within housing 240 and blood is drawn from a patient through port 138, around compressed positive displacement valve 120A and into the needleless syringe.

As the male luer is removed from port 250, positive displacement valve 120A resiliently expands to its original position (as shown) and reseals port 250 of housing 240.

Moreover, air channels 122 and 136, in combination, are filled with air when positive displacement valve 120A is in the uncompressed state. The air is dispelled out of needleless valve system 200 when positive displacement valve 120A moves from an uncompressed to compressed state. The air is recalled into needleless valve system 200 when positive displacement valve 120A moves from a compressed to uncompressed state, thereby, dispelling fluid through port 138 such that blood does not enter into housing 240 via the catheter.

Figure 3A:
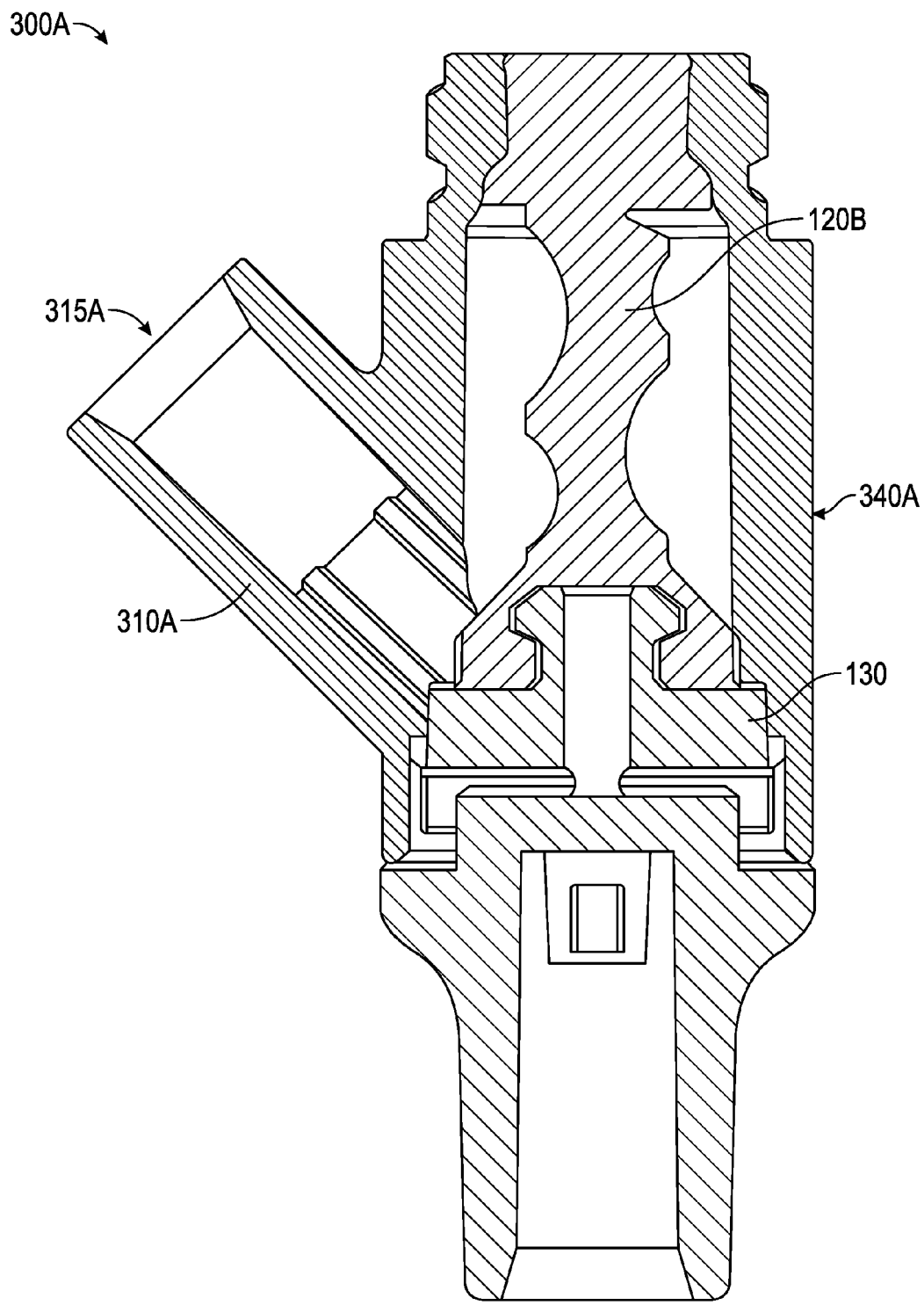
FIG. 3A illustrates an embodiment of a needleless valve system.
Figure 3B:
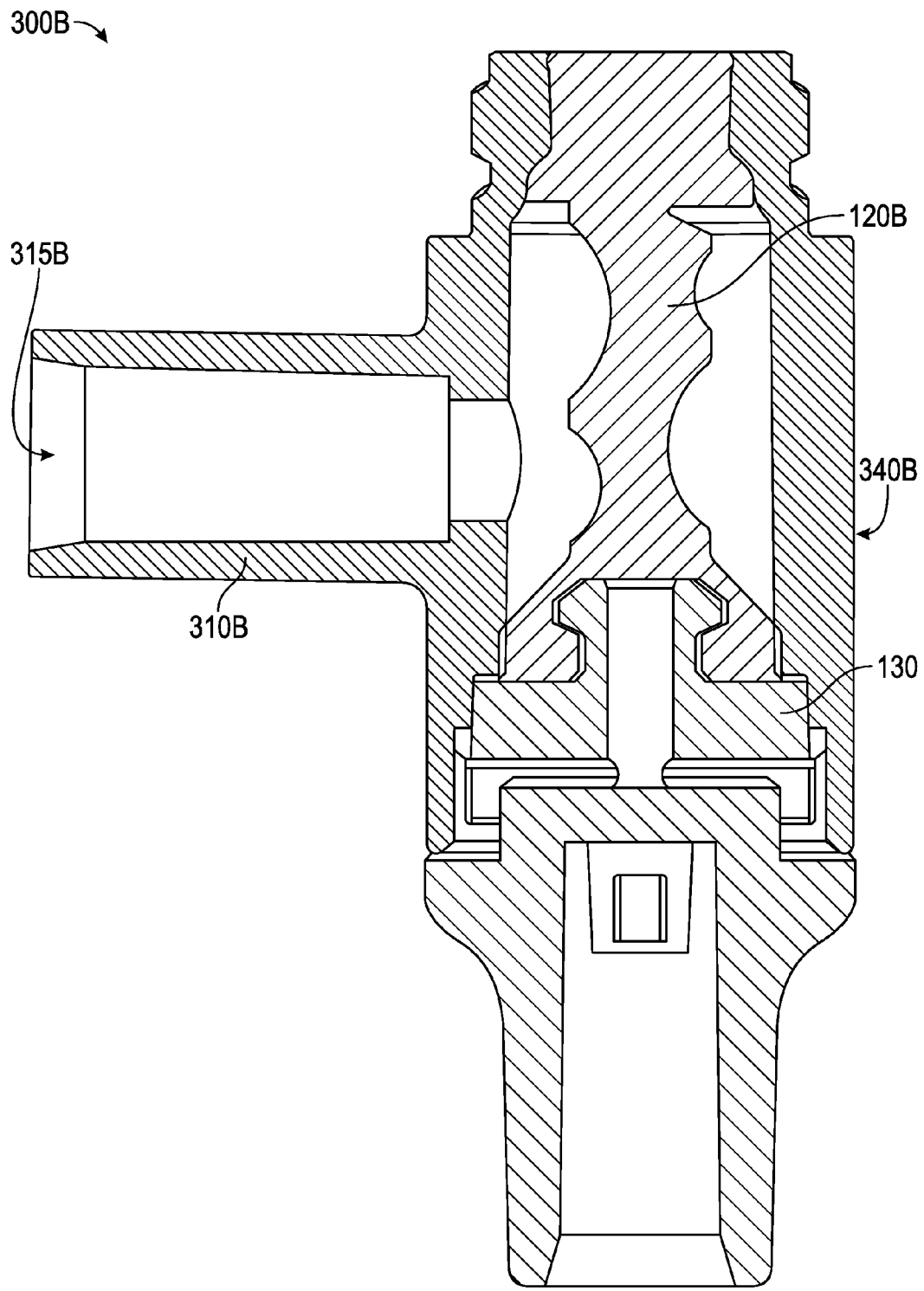
FIG. 3B illustrates an embodiment of a needleless valve system.

FIGS. 3A-B depicts embodiments of cross-sectional views of needleless valve systems 300A-B. Needleless valve systems 300A-B are similar to needleless valve system 200, as described above.

With reference to FIG. 3A, in one embodiment, needleless valve system 300A includes stem 310A that protrudes from housing 340A. In one embodiment, stem 310A protrudes from housing 340A to form a shape similar to a "Y." However, in various embodiments, stem 310A can protrude from any angle from housing 340A.

Port 315A is configured to allow conveyance of another fluid into housing 340A. For example, stem 310A is interfaces with a tube connected to an IV bag. Accordingly, fluid from the IV bag is able to flow through port 315A into housing 340A and subsequently to a patient.

Needleless valve system 300B is similar to needleless valve system 300A. However, in one embodiment, stem 310B protrude perpendicularly from housing 340B to form a "T" shape. However, in various embodiments, stem 310B can protrude from any angle from housing 340B.

Figure 4:
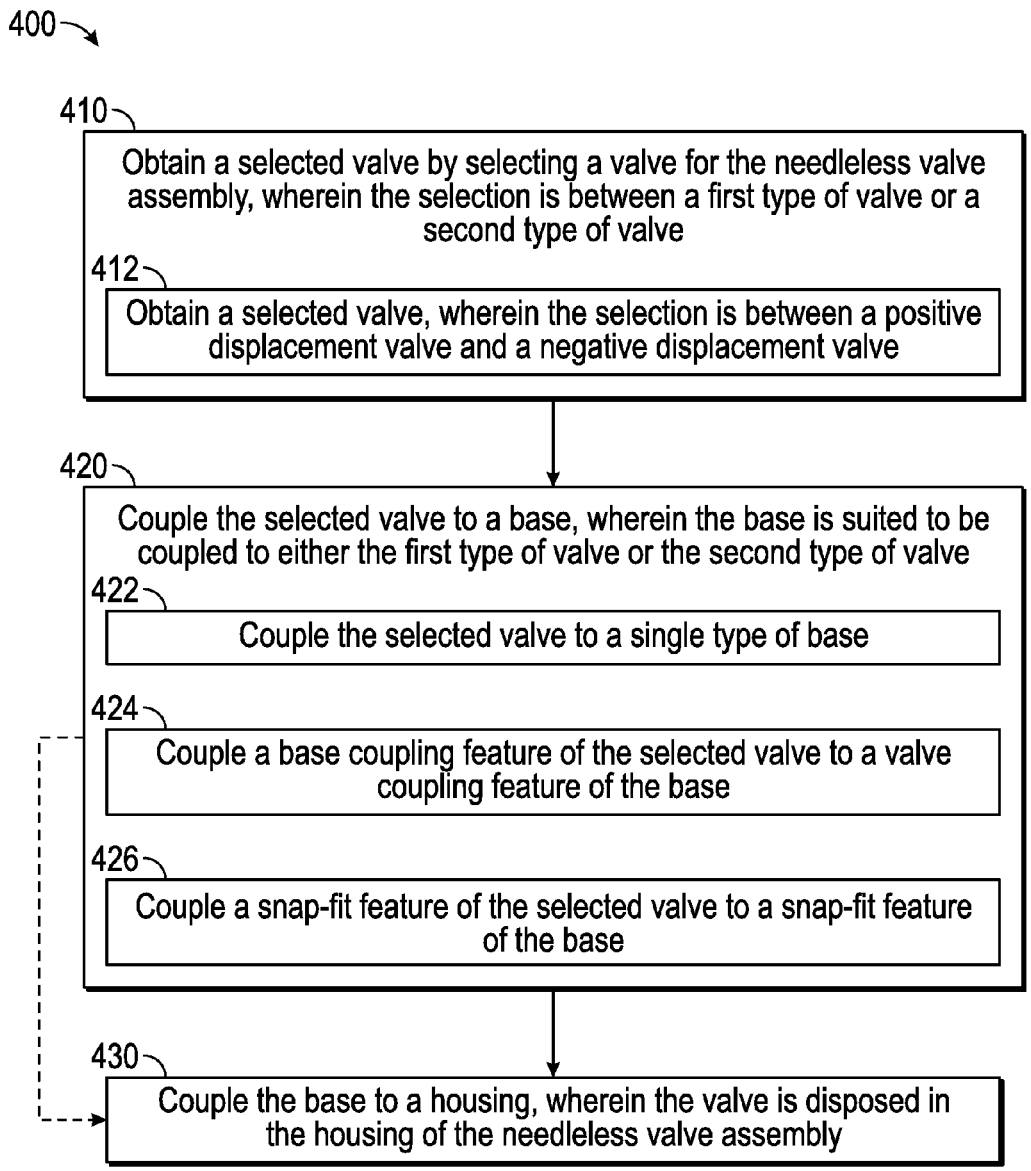
FIG. 4 illustrates an embodiment of a method for assembling a needleless valve system.

FIG. 4 depicts an embodiment of method 400 for assembling a needleless valve system.

At 410 of method 400, a selected valve is obtained by selecting a valve for the needleless valve assembly, wherein the selection is between a first type of valve or a second type of valve. For example, a manufacturer of needleless valve systems has an inventory of positive displacement valves (e.g., positive displacement valve 120A) for assembly of positive displacement needleless valve systems and an inventory of negative displacement valves (e.g., negative displacement valve 120B) for assembly of negative displacement needleless valve systems. In response to receiving an order for 500 positive displacement needleless valve systems, 500 positive displacement valves are obtained by selecting 500 positive displacement valves (rather than 500 negative displacement valves) to manufacture the 500 positive displacement needleless valve systems.

In particular, in one embodiment, at 412, a selected valve is obtained, wherein the selection is between a positive displacement valve (e.g., positive displacement valve 120A) and a negative displacement valve (e.g., negative displacement valve 120B).

At 420, the selected valve is coupled to a base, wherein the base is suited to be coupled to either the first type of valve or the second type of valve. For example, the selected valve (e.g., positive displacement valve 120A) is coupled to base portion 130, wherein base portion 130 is configured to be coupled to either a first type of valve (e.g., positive displacement valve 120A) or a second type of valve (e.g., negative displacement valve 120B).

In one embodiment, at 422, the selected valve is coupled to a single type of base. For example, base portion 130 is utilized for both the assembly of a positive displacement needleless valve systems and the assembly of negative displacement needleless valve systems. Therefore, either positive displacement valve 120A is coupled to base portion 130 or negative displacement valve portion 120B is coupled to base portion 130. In other words, two different types of base portions are not required to assemble a positive displacement needleless valve system and a negative displacement needleless valve system.

In another embodiment, at 424, a base coupling feature of the selected valve is coupled to a valve coupling feature of the base. For example, base coupling feature 125 is coupled to valve coupling feature 134.

In a further embodiment, at 426, a snap-fit feature of the selected valve is coupled to a snap-fit feature of the base. For example, the snap-fit feature of base coupling feature 125 is snapped around valve coupling feature 134.

At 430, the base is coupled to a housing, wherein the valve is disposed in the housing of the needleless valve assembly. For example, base portion 130 is coupled to housing 240, wherein positive displacement valve 120A is disposed in housing 240 of needleless valve assembly 200.

Various embodiments of the present invention are thus described. While the present invention has been described in particular embodiments, it should be appreciated that the present invention should not be construed as limited by such embodiments, but rather construed according to the following claims.

The invention claimed is:

1. A method for assembling a needleless valve system, said method comprising:
   obtaining a selected valve, wherein said selected valve is obtained by selecting a valve for said needleless valve system, wherein said selection is between a positive displacement valve or a negative displacement valve;
   coupling said selected valve to a base having an air channel, wherein said base seals with (i) a base coupling feature of said positive displacement valve, when coupled to a positive displacement valve, to pneumatically associate the base air channel and an air channel in the positive displacement valve, and (ii) a base coupling feature of said negative displacement valve, when coupled to a negative displacement valve, to pneumatically isolate the base air channel;

coupling said base to a housing, wherein said valve is disposed in said housing; and coupling a fitting to said housing such that a portion of said fitting engages said housing and said base is retained between said housing and said fitting.

2. The method of claim 1, wherein said obtaining a selected valve further comprises: obtaining a selected valve, wherein said selection is between the positive displacement valve and the negative displacement valve.

3. The method of claim 1, wherein said selection of said valve does not require a different type of base.

4. The method of claim 1, wherein said coupling said selected valve to a base, further comprises coupling said selected valve to a single type of base.

5. The method of claim 1, wherein said coupling said selected valve to a base, further comprises coupling a base coupling feature of said selected valve to a valve coupling feature of said base.

6. The method of claim 1, wherein said coupling said selected valve to a base, further comprises coupling a snap-fit feature of said selected valve to a snap-fit feature of said base.

7. A needleless valve system comprising:

a housing;

a fitting, wherein a portion of the fitting engages the housing; and a base portion comprising:

a body;

a valve coupling feature disposed on said body, wherein said valve coupling feature is configured to couple with a base coupling feature of a positive displacement valve and a base coupling feature of a negative displacement valve;

an interface feature comprising a port for conveying fluid, the interface feature disposed through the fitting while the base portion is retained in the housing by engagement between the fitting and the housing; and an air channel through the base;

wherein the valve coupling feature seals with (i) the base coupling feature of the positive displacement valve, when coupled to a positive displacement valve, to pneumatically associate the base air channel and an air channel in the positive displacement valve, and (ii) the base coupling feature of the negative displacement valve, when coupled to a negative displacement valve, to pneumatically isolate the base air channel.

8. The needleless valve system of claim 7, wherein said port is coaxial with the base air channel.

9. The needleless valve system of claim 7, wherein said valve coupling feature further comprises a snap-fit feature.

10. A needleless valve system comprising:

a valve, wherein said valve is a positive displacement valve or a negative displacement valve, wherein said valve comprises a base coupling feature;

a base portion comprising: a valve coupling feature coupled with said base coupling feature of said valve, an interface feature, and an air channel through the base, wherein the valve coupling feature seals with (i) the base coupling feature of the positive displacement valve, when coupled to a positive displacement valve, to pneumatically associate the base air channel and an air channel in the positive displacement valve, and (ii) the base coupling feature of the negative displacement valve, when coupled to a negative displacement valve, to pneumatically isolate the base air channel;

a housing, and a fitting, wherein a portion of the fitting engages the housing; and wherein said valve and base portion are retained within said housing by engagement between the fitting and the housing such that said interface feature is disposed through the fitting.

11. The base portion of claim 10, wherein said valve coupling feature further comprises a snap-fit feature.

12. The needleless valve system of claim 10, wherein said base coupling feature further comprises a snap-fit feature.

13. The needleless valve system of claim 10, wherein said base portion further comprises a port for conveying fluid.

14. The needleless valve system of claim 10, wherein said base portion is fluidly sealed to said housing.

\* \* \* \* \*